(12) United States Patent
Marrelli

(10) Patent No.: US 6,343,516 B1
(45) Date of Patent: *Feb. 5, 2002

(54) MULTIPHASE FLOW SAMPLING USING AN AUTOTRAVERSING SAMPLE PROBE

(75) Inventor: John D. Marrelli, Houston, TX (US)

(73) Assignee: Texaco Inc., White Plains, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/007,948

(22) Filed: Jan. 16, 1998

(51) Int. Cl.[7] .............................. G01F 1/74; G01N 29/02

(52) U.S. Cl. .................. 73/861.04; 73/23.28; 73/61.44; 73/863.56; 73/863.82

(58) Field of Search ........................... 73/861.04, 23.24, 73/23.28, 61.43, 61.44, 61.47, 863.41, 863.52, 863.56, 863.82

(56) References Cited

U.S. PATENT DOCUMENTS

| | | | | |
|---|---|---|---|---|
| 4,346,609 A | * | 8/1982 | Diesel | 73/863.51 |
| 4,442,120 A | * | 4/1984 | Apley et al. | 73/863.51 |
| 4,499,418 A | * | 2/1985 | Helms et al. | 324/58.5 A |
| 4,977,915 A | * | 12/1990 | Marrelli | 137/4 |
| 5,483,171 A | * | 1/1996 | Hatton et al. | 324/640 |
| 5,597,961 A | * | 1/1997 | Marrelli | 73/861.04 |
| 5,844,148 A | * | 12/1998 | Klein et al. | 73/863.82 |

* cited by examiner

Primary Examiner—Harshad Patel
(74) Attorney, Agent, or Firm—Morris N. Reinisch; Howrey Simon Arnold & White

(57) ABSTRACT

A system is provided for improved flow measurement in a multiphase fluid stream in an oilfield environment. A sampling probe is provided which draws fluid samples at different radial locations across a diameter or a chord of a cross sectional plane of a multiphase fluid flow line. Properties of these samples are measured by a multiphase flow metering system separately, and are then used to determine in a more accurate manner the fluid flow characteristics radially across the multiphase fluid flow line.

14 Claims, 2 Drawing Sheets

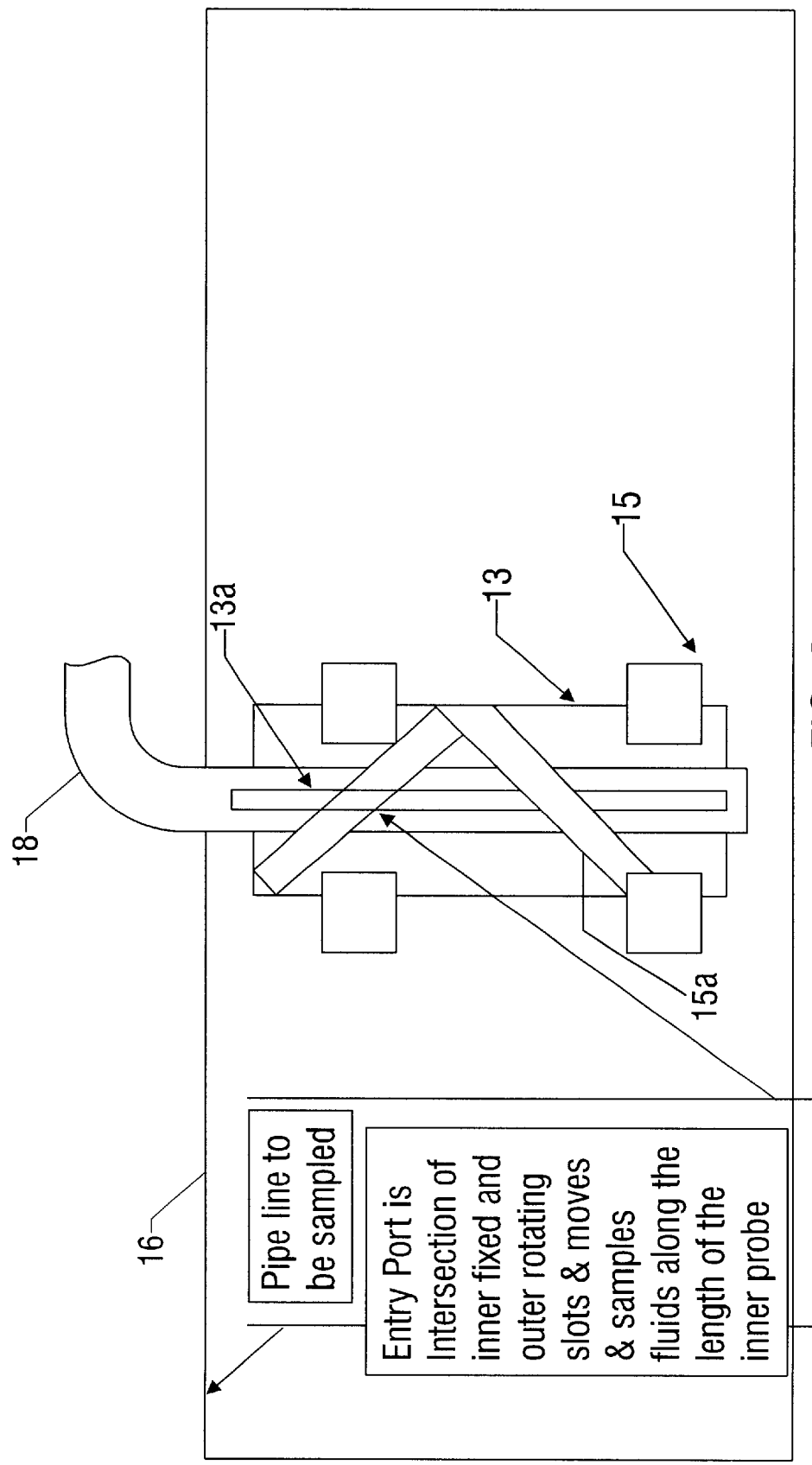

MULTIPHASE FLOW SAMPLING USING AN AUTOTRAVERSING SAMPLE PROBE

BACKGROUND OF INVENTION

1. Field of the Invention

The present invention relates to multiphase fluid flow, and more particularly, the measurement of gas fraction, water fraction and oil fraction in such systems wherein homogeneous flow of the fluid stream being measured is not obtainable. More particularly, the invention relates to a multiphase flow measuring system capable of selectively sampling fluid flow in a multiphase flow regime at different known points across the diameter of the flow line containing the fluid being measured. Also the invention relates to a sample probe which allows fluid sampling at different known points along the probe length. Also the invention relates to correction of pressure drop flow rate instrument for inhomogeneous flow.

2. The Prior Art

Recent advances in the measurement of multiphase fluid flow are typified in co-assigned U.S. Pat. No. 5,597,961. The Texaco STARCUT® watercut monitor used in such systems irradiates fluid flow samples with microwave energy and measures the reflected, transmitted, phase and intensity of the sample to derive quantitative measures of gas fraction, water fraction and hydrocarbon fraction in the flowing fluid stream. This type of system has proven to be very accurate in use in the oil industry throughout the world.

In most non-homogeneous flow regime cases it has been found that certain components of the total volumetric flow in a line are unevenly distributed across the diameter of a perpendicular cross section of the line as the fluid flows. Knowledge this uneven distribution is essential for accurate functioning of multiphase meters. For example density contract and distribution has been shown to be of major importance in orifice meters. The STARCUT® monitor is usually placed in a sidestream flowline in the manner depicted in the previously referenced patent. If the physical sampling point is at the outer diameter or the inner diameter of the flow line being measured, an inaccurate measurement could result in an inhomogeneous multiphase fluid flow regime. There have been attempts in the prior art to make selective, radial samples in measuring this type of flow regime.

In co-assigned U.S. Pat. No. 4,977,915 the effectiveness of a demulsifier injection rate is evaluated using two sample points in a flowing multiphase stream caused to go around a bend to develop a density gradient along its radius. The STARCUT® monitor samples the flowing multiphase stream at two different radial positions along a cross section of the flow to measure the density gradient so generated and therefore appraise the effectiveness of the demulsifier treatment.

In co-assigned U.S. Pat. No. 5,234,012 a multiphase flow stream is divided in two and a STARCUT® watercut monitor is used to measure separately the flow in each stream, being installed in each branch of the divided flow lines as a sidestream monitor.

While such attempts to monitor non-homogeneous multiphase flow regimes have been successful to various degrees, none has been completely satisfactory.

BRIEF DESCRIPTION OF THE INVENTION

There is a need to improve side stream sampling in a system using the STARCUT® watercut monitor to allow fluid composition determination at several radially dispersed locations across the diameter of a cross section of the flow line. The present invention provides such a system. A sampling probe is provided for drawing fluid samples at different radial locations across a diameter or chord of a cross section of the flow line. The entry port (inlet) of the sidestream sample probe is formed by the intersection of two slots, one a stationary longitudinally disposed slot, and the second a helically shaped slot cut in a cylinder rotating about the central axis of the stationary probe having the diametrically disposed slot. The slot may be shaped to provide a sample port shape. For example the longitudinal slot sides may be parallel or non-parallel. The helical slot may also be of non-parallel or parallel sides. The intersection hole size at any point along the sample length is therefore controlled by the slot shapes. As the rotating cylinder turns, the intersection of the two slots moves across the diameter or chord of the plane of the cross section of the flow line in which the diametrically disposed slot line is located. This provides complete sampling of the flow from one edge of the flow line (or pipe's inner diameter or chord) to the opposite end. As the STARCUT® watercut monitor is capable of making multiple (more than 300) measurements per second, an improved measurement of the true gas, water and oil fractions of fluid in the multiphase line, even in a inhomogeneous flow regime is provided.

The rotation can be motor driven or flow driven. In general the location of the moving slot intersection is required to interpret the sample data in terms of fluid distribution in the pipeline. The intersection location is typically determined by use of conventional auto correlation methods, that is by using the inherent patterning in the sample signal. This pattern is referenced to the wall by using one of several methods: 1.) use of a switch on the rotating component to indicate start at one wall, 2.) by use of a model which extends pattern shape relative to wall.

Slot hole size and shape is important for sampling rate control. For example, the hole size may be sized to give a hole which is larger near the walls of the pipeline then in the center. In vertical flow axial symmetry of fluid properties may be assumed to be statistically valid. Fluid samples in vertical flow, for example, at the walls statistically represent volume of pipeline liquid which is greater than fluid samples at the center. In a preferred embodiment discussed herein the sample hole area is to be proportional to the distance from pipeline center. This size relation to pipe portion will give the proportional sampling value. Also the fluid velocity entering the sample probe must be greater than sample hole velocity to insure fluids stuck in the probe in the order in which they exist in the pipe. Fluid samples within the probe line to the fluid sampler detector will also blend together some what. Statistical averaging and short probe line will minimize sample blending.

The invention is best understood by reference to the following detailed description thereof, when taken in conjunction with the accompanying drawings. The drawings are intended as illustrative only and not as limitative.

BRIEF DESCRIPTION OF THE DRAWINGS

FIG. 2 is a highly schematic view, partially in section, showing more detail of the sampling probe in the system of the invention.

DESCRIPTION OF THE PREFERRED EMBODIMENTS

Figure 1:
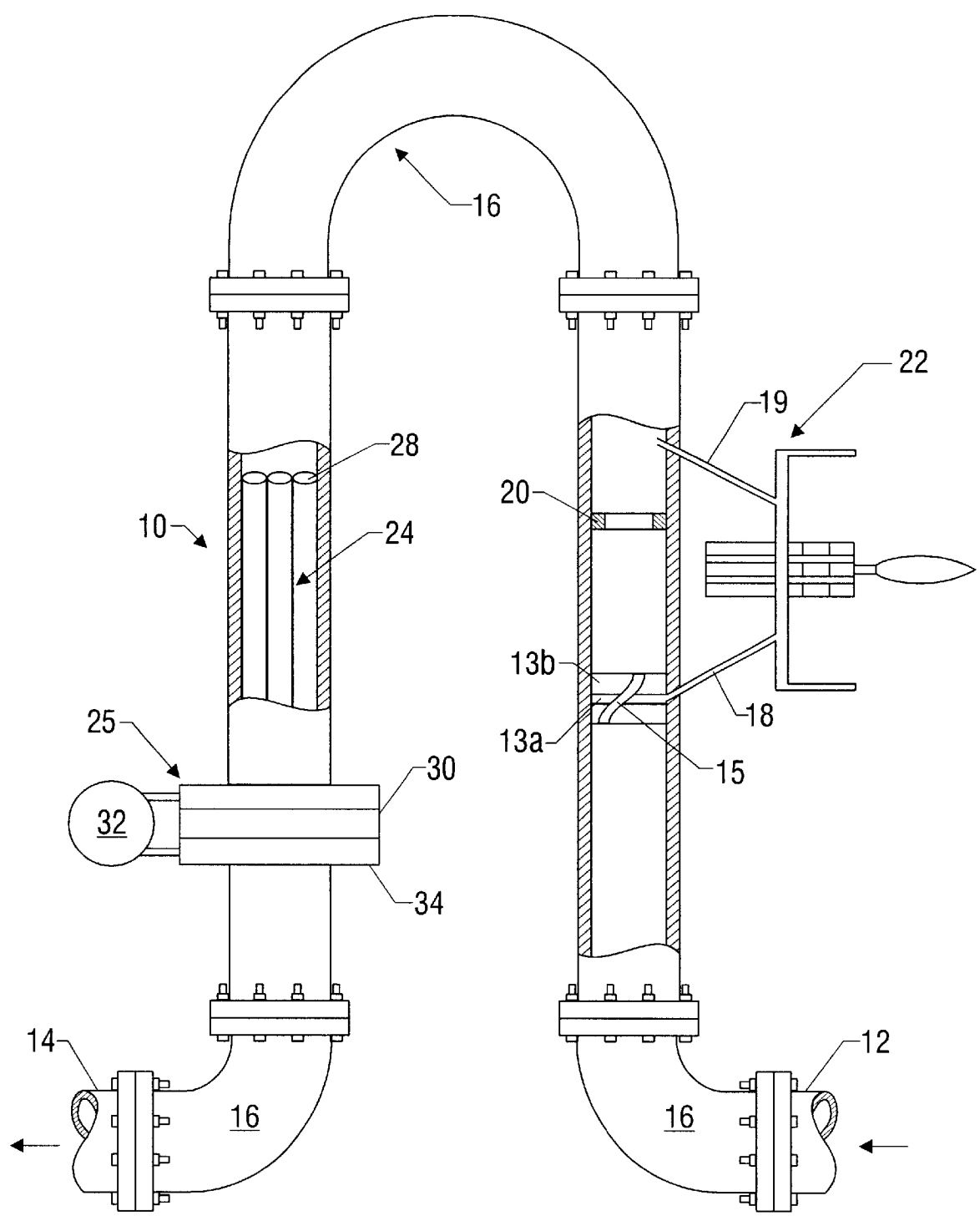
FIG. 1 is highly schematic view partially in section, showing a STARCUT® watercut monitor based system for multiphase flow measurement sing the sidestream sampling probe according to concepts of the invention.

Referring initially to FIG. 1 a multiphase flow line shown generally at 16 is provided with a Texaco STARCUT® watercut monitor shown generally at 22. This monitor is shown in more detail and its operation explained in U.S. Pat. Nos. 4,499,418 and 4,947,127 which are incorporated herein by reference.

The inlet pipe 12 of flow line 16 routes the multiphase fluid across an orifice plate 20, which provides a pressure drop between monitor 22 input line 18 and its output line 19. The entrance or inlet to line 18 comprises components 13, 13A and 15 which will be explained in more detail subsequently. In the outlet left of flow line 16 is a flow straightener 24 and a differential flow meter 26 having an orifice plate 30. The flow straightener 24 comprises a bundle of smaller diameter straight pipes 28. Flow meter 26 has orifice plate 30 and differential pressure meter 32 placed across plate 30. These devices function as disclosed in previously mentioned U.S. Pat. No. 5,597,961 to measure the three phase (oil, water, gas) flow components passing through monitor 22 in the manner described therein. This patent is also incorporated by reference herein.

The sample input line 18 is provided on its interior to flow line 16 with a diametrically disposed longitudinal slot 13A. Mounted on bearings, (not shown), to the interior portion of input line 18 is a cylindrical rotating collar 13B. The cylindrical collar 13B is provided with a set of fins 15, as shown more clearly in FIG. 2, to promote the rotation of collar 13B in the moving fluid stream in flow line 16. As the longitudinal slot 13A in the probe input line 18 is only cut on one side thereof (i.e. the downstream side preferably), the effective entrance aperture of input line 18 (inlet to monitor 22) is covered except for the portion thereof at the intersection of slot 13A and slot 15A. Slot 15A is a generally helically shaped slot which makes one complete revolution in the length of the collar 13B as it spans the interior diameter or chord of pipe 16. In place of the simple fins 15 as shown, turbine blades or the like could be used on the exterior of the collar 13B or could be motor driven by an electric motor, if desired. It is also apparent that the shape or pitch of the generally helical slot 13A in collar 13B could be varied to control the movement of the effective entrance to input line 18 diametrically across the interior diameter or chord of flow line 16 across which the probe is placed.

Several advantages occur in inhomogeneous flow regime measurements made with the present system. The sample of fluid is "scanned" diametrically at a rate proportional to its flow rate. Moreover, a particular location along the diameter or chord of flow line 16 from which the data is taken can deduced from the data. The time and spatial averaging of many "scans" is possible which allows high signal to noise ratio and the development of average flow profiles for the line being measured. Finally, the monitoring of such inhomogeneous fluid flow regimes over the long term reveal hitherto unknown fluid flow principles.

The flow rate determination through an orifice is a function of pressure drop when average density of the fluid is constant across the plane of the orifice. Typically in vertical flow low density components such as gas and oil will tend to locate closer to the flow axis. Our invention provides a density index with which the average density to flow rate relationship is modified to account for inhomogenety in density. A simple density index di is the average density slope from wall to center of pipe. Using the density index di, flow rate, Q, through an orifice is $Q=\sqrt{dp(1+di)}$ where dp is the pressure differential across the orifice.

The foregoing descriptions may make other alternative arrangements apparent to those of skill in the art. The aim of the appended claims is to cover all such changes and modifications that fall within the true spirit and scope of the invention.

What is claimed is:

1. A system for determining the volumetric flow rates of the oil/water/gas fractions of multiphase fluid flow in a fluid flow line at each location in a line perpendicular to the flow line parallel to a chord or diameter of said flow line, comprising:

a continuous flow watercut monitor placed as a sidestream monitor having an inlet side and an outlet side disposed across an orifice plate in a multiphase fluid flow line, and capable of continuously measuring and providing three separate continuous output signals representative of the oil fraction, the gas fraction and the water fraction of fluid flow in said flow line;

means for measuring continuous pressure drop over a constriction of the sample line; and means for moving the physical location of the entrance to said inlet side of said watercut monitor radially along a chord or diameter of a cross sectional plane of said flow line.

2. The system of claim 1 wherein said means for moving the physical location of the entrance to said inlet side comprises a cylindrical tube connected to said inlet side, and having a slot cut longitudinally along one side thereof, and said longitudinal slot being disposed along a chord or diameter of a cross sectional plane of said flow line, and wherein said means for moving the physical location of the entrance to said inlet side has an opening along only a portion of the length of said slot at any instant to the flow of fluid in said flow line.

3. The system of claim 2 wherein said means for moving the physical location of the entrance to said inlet side includes a rotatably mounted second cylinder having a wall and mounted coaxially with said cylindrical tube, and said second cylinder having its cylindrical wall cut by a predetermined shaped slot cut therein.

4. The system of claim 3 wherein said predetermined shaped slot comprises a generally helically shaped slot.

5. The system of claim 4 wherein said generally helically shaped slot has a pitch of one complete revolution along the length of said second cylinder.

6. The system of claim 5 wherein said longitudinal slot is shaped to be wider at the wall of the pipeline than at the center of the pipeline.

7. The system of claim 1 wherein average fluid density and radial fluid density are determined in a pressure drop meter.

8. The system of claim 7 wherein radial fluid density is used to correct the average fluid density prediction of flow rate by said pressure drop meter.

9. A system for determining the volumetric flow fractions of the oil/water/gas fractions of multiphase fluid flow in a fluid flow line at each location in a line perpendicular to the flow line parallel to a chord or diameter of said flow line, comprising:

a continuous flow watercut monitor placed as a sidestream monitor having an inlet side and an outlet side disposed across an orifice plate in a multiphase fluid flow line, and capable of continuously measuring and providing three separate continuous output signals representative of the oil fraction, the gas fraction and the water fraction of fluid flow in said flow line;

means for measuring continuous pressure drop over a constriction of the sample line; and means for moving the physical location of the entrance to said inlet side of said watercut monitor radially along a chord or diameter of a cross sectional plane of said flow line.

10. The system of claim 9 wherein said means for moving the physical location of the entrance to said inlet side comprises a cylindrical tube connected to said inlet side and having a slot cut longitudinally along one side thereof and said longitudinal slot being disposed along a chord or diameter of a cross sectional plane of said flow line, and wherein said means for moving the physical location of the entrance to said inlet side has an opening along only a portion of the length of said slot at any instant to the flow of fluid in said flow line.

11. The system of claim 10 wherein said means for effectively moving the physical location of the entrance to said inlet side includes a rotatably mounted second cylinder having a wall and mounted coaxially with said cylindrical tube, and said second cylinder having its cylindrical wall cut by a predetermined shaped slot cut therein.

12. The system of claim 11 wherein said predetermined shaped slot comprises a generally helically shaped slot.

13. The system of claim 12 wherein said generally helically shaped slot has a pitch of one complete revolution along the length of said second cylinder.

14. The system of claim 13 wherein said longitudinal slot is shaped to be wider at the wall of the pipeline then at the center of the pipeline.

* * * * *